US008318223B2

(12) United States Patent
Miwa (10) Patent No.: US 8,318,223 B2
(45) Date of Patent: Nov. 27, 2012

(54) METHOD FOR PRODUCING MODIFIED MILK (75) Inventor: Noriko Miwa, Kanagawa (JP)

(73) Assignees: Ajinomoto Co., Inc., Tokyo (JP);
Amano Enzyme Inc., Nagoya-shi (JP)

( * ) Notice: Subject to any disclaimer, the term of this patent is extended or adjusted under 35 U.S.C. 154(b) by 0 days.

(21) Appl. No.: 13/074,081

(22) Filed: Mar. 29, 2011

(65) Prior Publication Data
US 2011/0236529 A1 Sep. 29, 2011

Related U.S. Application Data (63) Continuation of application No. PCT/JP2009/066754, filed on Sep. 28, 2009.

(30) Foreign Application Priority Data

Sep. 29, 2008 (JP) ................................ 2008-250111

(51) Int. Cl.
*A23C 9/12* (2006.01)
(52) U.S. Cl. ................ 426/34; 426/36; 426/42; 426/43; 426/580
(58) Field of Classification Search .................... 426/34, 426/36, 42, 43, 580, 582, 583, 587
See application file for complete search history.

(56) References Cited

U.S. PATENT DOCUMENTS

| 3,857,967 | A | * | 12/1974 | Kikuchi et al. ................. 426/18 |
| 6,756,221 | B1 | * | 6/2004 | Yamaguchi .................... 435/227 |
| 7,008,653 | B2 | | 3/2006 | Matsumura et al. |
| 7,947,315 | B2 | * | 5/2011 | Kodera et al. ................... 426/36 |
| 2005/0244542 | A1 | | 11/2005 | Florin-Christensen et al. |
| 2007/0254065 | A1 | | 11/2007 | Kodera et al. |
| 2007/0254066 | A1 | | 11/2007 | Miwa et al. |
| 2008/0038405 | A1 | | 2/2008 | Marchenko et al. |
| 2010/0151081 | A1 | | 6/2010 | Tams et al. |
| 2011/0064847 | A1 | | 3/2011 | Miwa et al. |

FOREIGN PATENT DOCUMENTS

| DE | 2 044 866 | 3/1972 |
| JP | 2000-50887 A | 2/2000 |
| JP | 2001-218590 A | 8/2001 |
| JP | 2003-250460 A | 9/2003 |
| JP | 2006-515512 A | 6/2006 |
| JP | 2008-509698 A | 4/2008 |
| WO | WO 02/068671 A1 | 9/2002 |
| WO | WO 2006/075772 A1 | 7/2006 |
| WO | WO 2007/141385 A1 | 12/2007 |
| WO | WO 2008/138900 A2 | 11/2008 |

OTHER PUBLICATIONS

U.S. Appl. No. 12/970,049, filed Dec. 16, 2010, Miwa et al.
International Search Report issued Dec. 22, 2009 in corresponding International Application No. PCT/JP2009/066754 (with an English Translation).
Shotaro Yamaguchi et al., "A Novel Protein-Deamidating Enzyme from *Chryseobacterium proteolyticum* sp. nov., a Newly Isolated Bacterium from Soil", Applied and Environmental Microbiology, Aug. 2000, vol. 66, No. 8, pp. 3337-3343.
Shotaro Yamaguchi et al., "Protein-Glutaminase from *Chryseobacterium proteolyticum*, an Enzyme that Deamidates Glutaminyl Residues in Proteins", Eur. J. Biochem., 2001, vol. 268, pp. 1410-1421.
Y. S. Gu et al., "Action of Protein-Glutaminase on α-Lactalbumin in the Native and Molten Globule States", J. Agric. Food Chem., 2001, vol. 49, pp. 5999-6005.
Kunio Yamauchi, "Comprehensive Encyclopedia of Milk", Asakura Shoten, p. 60.
G. A. H. De Jong et al., "Transglutaminase Inhibitor from Milk", Journal of Food Science: Food Chemistry and Toxicology, 2003, vol. 68, No. 3, pp. 820-825.
Tomohiro Noguchi, "Yoghurt Seihin no Gyokosei ni Taisuru Atarashii Approach ~ Dasshifunnyu no Kanetsu Henseido no Eikyo~", Chikusanbutsu Jukyu Kankei Gakujutsu Kenkyu Joho Shushu Suishin Jigyo Hokokusho Heisei 17 Nendo, 2006, vol. 37, pp. 39-44.
European Search Report issued in Application No. 09816239.9 on Mar. 23, 2012.

* cited by examiner

*Primary Examiner* — Leslie Wong
(74) *Attorney, Agent, or Firm* — Oblon, Spivak, McClelland, Maier & Neustadt, L.L.P.

(57) ABSTRACT

Provided is a method whereby a dairy product having a rich and creamy texture can be obtained by reducing or removing a reaction inhibitor of a protein deamidating enzyme contained in a raw material milk having low heat history to thereby more efficiently and more effectively treat the raw material milk having low heat history with a protein deamidating enzyme. A raw material milk having low heat history is treated with a protein deamidating enzyme after or simultaneously with a treatment, such as an addition of a calcium chelating agent, for reducing a protein deamidating enzyme inhibitor.

32 Claims, 6 Drawing Sheets

METHOD FOR PRODUCING MODIFIED MILK

CROSS REFERENCES TO RELATED APPLICATIONS

This application is a continuation of International Patent Application No. PCT/JP2009/066754, filed on Sep. 28, 2009, and claims priority to Japanese Patent Application No. 2008-250111, filed on Sep. 29, 2008, both of which are incorporated herein by reference in their entireties.

BACKGROUND OF THE INVENTION

1. Field of the Invention

The present invention relates to a methods for producing modified milk. The present invention further relates to methods for producing a dairy product using such a modified milk.

2. Discussion of the Background

Raw milk (milk fresh from a cow) lends our everyday meals affluence by being processed into various kinds of dairy products, as well as for drinking as a milk, such as an ice cream, yoghurt, cheese, powdered milk, lactic acid bacteria beverage, and the like made from milk or butter made from cream separated from raw milk.

One of the most efficient indicators for determining "tastiness" of such dairy products is dense and creamy texture of milk fat and it is said that the texture has a close relation with fat content of the dairy products. On the other hand, recently, an attention to easiness to purchase such as a "low-price" product and the like, or to health for consumers such as a "low-calorie" product and the like, is increasing as a factor for determining a commercial value. Although various kinds of dairy products containing less milk fat content, such as no fat products or low fat products, are developed according to the increasing demands, the taste of these products is still plain, watery and less milk flavor, and therefore consumers were not satisfied. Thus it is required to develop tasty dairy products that can satisfy consumers' demands even when milk fat content is low or without increasing milk fat content.

By the way, nowadays enzymes are utilized in various fields in a food industry. The merits of using enzymes are given that an enzyme acts only on specified material under mild conditions and that an influence on taste is small. Developments and improvements of foods or improvements of manufacturing processes are carried out for various purposes by utilizing such superior characteristics of enzymes.

Among them, a protein deamidating enzyme is attracting our attention as a new enzyme for giving dense and creamy texture, which can be obtained when milk fat is added, to dairy products. The enzyme is a catalytic enzyme that facilitates a deamidating reaction by acting on a glutamine residue in a protein and it is also referred to as a protein glutaminase (hereinafter designated as "PG"). The glutamine residue in a protein is converted into glutamic acid residue and produces carboxylic group, and therefore increasing of negative charge, increasing of electrostatic repulsion, decreasing of isoelectric point, increasing of hydrating power, and the like occur in the protein. It is known that, as a result, improvement of various kinds of functional characteristics can be obtained such as increasing of solubility and dispersing ability in water, increasing of emulsificating ability and stability, and the like, of the protein (see, Japanese Patent Kokai Publication No. JP-P2000-50887A; Japanese Patent Kokai Publication No. JP-P2001-218590A; Yamaguchi et al., *Appl. Envi- ron. Microbiol.*, vol. 66, pp. 3337-3343 (2000); Yamaguchi et al., *Eur. J. Biochem.*, vol. 268 pp. 1410-1421 (2001); Matsumura et al., *J. Agric. Food Chem.*, (2001), vol. 49, pp. 5999-6005; and *Comprehensive Encyclopedia of Milk*, edited by Kunio Yamauchi, Asakura Shoten, p. 60, 1992, which are incorporated herein by reference in their entireties). It is also known that PG having such characteristics improves the smooth texture of dairy products such as yoghurt or cheese by using PG for such products (see, *Comprehensive Encyclopedia of Milk*, edited by Kunio Yamauchi, Asakura Shoten, p. 60, 1992, which is incorporated herein by reference in its entirety). Thus it is expected that PG may provide the dense and creamy texture that the milk inherently possesses even when the fat content in a dairy product was lowered.

Milk proteins contained in milk, the content of which is 3.0 to 3.5%, are classified into two large groups, one is casein and the other is whey protein. Casein amounts to about 80% of the total protein and whey protein amounts to about 20% of the total protein. Casein is made up of four components of $\alpha s1$-casein, $\alpha s2$-casein, $\beta$-casein and $\kappa$-casein, and whey protein is made up of $\alpha$-lactalbumin and $\beta$-lactglobulin.

At present, some reports can be seen that relate to PG action on such milk proteins. Yamaguchi et al., *Appl. Environ. Microbiol.*, vol. 66, pp. 3337-3343 (2000), which is incorporated herein by reference in its entirety, discloses that the reactivity of PG with $\alpha$- and $\beta$-casein is high and the reactivity of PG with $\alpha$-lactalbumin and $\beta$-lactglobulin is low. Matsumura et al., *J. Agric. Food Chem.* (2001), vol. 49, pp. 5999-6005 and WO2002/068671, which are incorporated herein by reference in their entireties, disclose that the reactivity of PG with $\alpha$-lactalbumin in the molten globule state, that is, during intermediate state in denaturation process of a protein, increases as compared with non-denaturation state.

It is not too much to say that the reactivity of PG with milk depends on the reactivity of casein, which amounts to the most part of milk, rather than the reactivity of whey protein. The most part of casein is dispersed in milk in the form of colloidal particles that are called as casein micelle whose diameter is 0.05 to 0.3 microns and mean diameter is about 0.1 microns. In addition, it is known that thermally sensitive whey protein interacts with the casein micelle (especially $\kappa$-casein that covers a surface of the casein micelle) by heating (see, *Comprehensive Encyclopedia of Milk*, edited by Kunio Yamauchi, Asakura Shoten, p. 60, 1992, which is incorporated herein by reference in its entirety).

However, the disclosures of Yamaguchi et al., *Appl. Environ. Microbiol.*, vol. 66, pp. 3337-3343 (2000); Matsumura et al., *J. Agric. Food Chem.* (2001), vol. 49, pp. 5999-6005; and WO2002/068671, which are incorporated herein by reference in their entireties, are results of research at an experimental reagent level and nothing is referred to for reactivity of the whole milk as a raw material of dairy products. It is speculated that the reactivity of PG in a complicated milk system as disclosed in *Comprehensive Encyclopedia of Milk*, edited by Kunio Yamauchi, Asakura Shoten, p. 60, 1992, which is incorporated herein by reference in its entirety will differ from that in a single component of milk protein; however, the reactivity of PG in milk has not been reported.

SUMMARY OF THE INVENTION

The following analyses are given by the present invention.

Under the background described above, the inventors of the present invention have developed the utilization of PG for dairy products. During the development, the inventors have found a problem that "the reactivity of PG to raw material milk having low heat history is small" for the first time. For example, the inventors have found that, comparing two kinds of milk, one is milk sterilized by low temperature and long time sterilization (LTLT method) (hereinafter called as "LTLT milk") and the other is milk sterilized by ultra-high temperature heating sterilization (UHT method) (hereinafter called as "UHT milk"), the former reacts only about two to three tenths compared with the latter with the same amount of enzyme. This means that the LTLT milk needs a greater amount of enzyme to obtain the same effect by the enzyme treatment as the UHT milk, and it may cause concern of high cost.

The difference of PG activity caused by heat history of raw material milk may limit the applicability of enzymes to dairy products and thus the technique of using enzymes cannot be an easy method for use for dairy products processors. That's because all of the raw material milk for dairy products cannot be necessarily sterilized by the UHT method from the view point of flavor or physical properties.

The inventors of the present invention then conducted research on the causes of the low reactivity of PG to a raw material milk with low heat history. Based on the research, the inventors have found that there is a PG inhibitor in a raw material milk of low heat history and the inhibitor causes the low reactivity of PG. Thus it has become a problem to find out a method to reduce or remove the inhibitor of PG existing in the raw material milk.

Until now, it is known (see, G. A. H De Jong et al., *Journal of Food Science*, vol. 68, Nr. 3, (2003) pp. 820-825, which is incorporated herein by reference in its entirety) that there exists in milk an inhibitor of transglutaminase, which is a protein cross-linking enzyme, but an inhibitor of PG was not known. Because PG is a new enzyme that was found recently, information from previous research is little. In addition, because PG is different from TG from the viewpoint of origin, primary sequence of protein, molecular weight, structure and various characteristics such as a catalytic function, and so on, it was supposed that an inhibition mechanism different from that of TG would contribute. Thus additional work was necessary for the problem.

The present invention has been made to solve the problem above mentioned and it is an object of the present invention to provide a method for producing a dairy product having good physical properties and texture (especially texture like fat) by reducing or removing a reaction inhibitor of protein deamidating enzyme (PG) existing in a raw material milk having low heat history and treating the raw material milk having low heat history with PG more efficiently and more effectively.

As a result of vigorous effort for achieving the object mentioned above, the inventors have found that there exists a PG reaction inhibitor in a fraction of low molecule (molecular weight of 10,000 or less) in milk having low heat history such as raw milk, LTLT sterilized milk, HTST sterilized milk, and the like. In addition, the present inventors have found that even the raw material milk having low heat history can be treated with PG efficiently and effectively by reducing or removing the PG reaction inhibitor using a process of heat processing (heating a raw material milk so as to control denaturation degree of whey proteins in the raw material milk in the range of 40 to 80%), an addition of a calcium chelating agent, an addition of an alkaline material (so as to adjust pH of the raw material milk in the range of 7 to 8), an addition of a reducing agent, or removal of a low molecule fraction. In addition, the inventors have found that milk of low heat history can be treated with PG efficiently and effectively by adding PG to milk of low heat history and treating at 60 to 65° C. By using the PG-modified milk obtained by aforementioned method as a raw material, dairy products having good physical properties and texture (especially fat-like texture) can be produced.

Thus, the present invention provides:

(1) A method for producing modified milk, comprising: a step of treating a raw material milk of raw milk, LTLT sterilized milk or HTST sterilized milk to reduce an inhibitor of a protein deamidating enzyme; and a step of further treating the raw material milk with a protein deamidating enzyme.

(2) The method of (1) above described, in which the treating to reduce an inhibitor of a protein deamidating enzyme is an addition of a calcium chelating agent to the raw material milk in an amount of 0.2 to 1.0 g per 100 g of the raw material milk.

(3) The method of (2) above described, in which the calcium chelating agent is sodium citrate, sodium γ-polyglutamate, or tetrasodium ethylenediamine-tetraacetate.

(4) The method of (1) above described, in which the treating to reduce an inhibitor of a protein deamidating enzyme is an addition of an alkaline material to the raw material milk in an amount of 0.01 to 0.5 g per 100 g of the raw material milk.

(5) The method of (4) above described, in which the alkaline material is sodium hydroxide, potassium carbonate, sodium carbonate, trisodium phosphate, sodium hydrogencarbonate, calcined calcium, or arginine.

(6) The method of (1) above described, in which the treating to reduce an inhibitor of a protein deamidating enzyme is an addition of a reducing material to the raw material milk in an amount of 0.0001 to 0.1 g per 100 g of the raw material milk or an addition of yeast extract containing a reducing agent in an amount of 0.0001 to 0.1 g per 100 g of the raw material milk.

(7) The method of (6) above described, in which the reducing material is glutathione, cysteine, or γ-glutamilcysteine.

(8) The method of (1) above described, in which the treating to reduce an inhibitor of a protein deamidating enzyme is removing a low molecule fraction, a molecular weight of which is 10,000 or less, from the raw material milk.

(9) The method of (8) above described, in which the removal of a low molecule fraction is performed using an ultrafiltration membrane.

(10) A method for producing modified milk, comprising: adding a protein deamidating enzyme to a raw material milk of raw milk, LTLT sterilized milk or HTST sterilized milk; and treating the raw material milk with a protein deamidating enzyme at 60 to 65° C.

(11) A method for producing a dairy product, by using the modified milk obtained by one of the methods of (1) to (10) above described.

(12) The method of (11) above described, in which the dairy product is yoghurt, cheese-like food, pudding, or milk-based drink.

According to the present invention, it is possible to obtain modified milk by treatment with a protein deamidating enzyme efficiently even from a raw material milk having low heat history, which has low reactivity with a protein deamidating enzyme. In addition, it is possible to produce dairy products having dense and creamy texture by using the modified milk as a raw material.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The present invention will now be described in detail. A producing method of modified milk according to the present invention is to treat a raw material milk having low heat history such as raw milk, LTLT milk, HTST milk and the like so as to reduce an inhibitor of a protein deamidating enzyme and treat the raw material milk with a protein deamidating enzyme. As to the sequence of the treating step for reducing a PG inhibitor and the treating step for treating the raw material milk with PG, it is possible to treat a raw material milk at first to reduce a PG inhibitor and then treat the raw material milk with PG, to treat a raw material milk with PG during treating the raw material milk for reducing a PG inhibitor, or to treat raw material milk for reducing a PG inhibitor during treating the raw material milk with PG. For example, when adding a calcium chelating agent, an alkaline material or a reducing agent for decreasing a PG inhibitor, it is possible to add the calcium chelating agent, alkaline material, reducing agent and PG to a raw material milk at the same time or to add the one at first and then add the other.

The raw material milk of raw milk, LTLT sterilized milk, or HTST sterilized milk used for the present invention means unprocessed raw milk obtained by milking an animal such as a cow or goat, milk obtained by LTLT or HTST sterilizing of raw milk, mixed milk thereof, defatted or partially defatted milk thereof, or processed milk thereof. Raw milk means milk as milked, that is, unprocessed milk. The LTLT sterilized milk means sterilized milk by a low-temperature long time sterilization method (LTLT method), and in concrete terms, milk sterilized at 62 to 66° C. for 30 minutes or sterilized at 75° C. or more for 15 minutes or more. The HTST sterilized milk, which is sterilized at 72 to 75° C. for 15 seconds, has a sterilizing effect almost the same as the LTLT method. The defatted milk means milk from which most fat component is removed and partially defatted milk is that fat component is partially removed.

An effective treatment to reduce an inhibitor of a protein deamidating enzyme according to the present invention is an addition of a calcium chelating agent, an addition of an alkaline material, an addition of a reducing agent, fractionation and removal of low molecule fraction, or using a temperature at 60 to 65° C. for the enzyme reaction. It is possible to obtain PG reactivity at the same level as that with UHT milk by controlling a heating condition such that the range of denaturation degree of whey proteins in a raw material milk becomes 40 to 75%.

When adding a calcium chelating agent, the amount of addition is preferably 0.05 to 0.5 g, more preferably 0.4 to 1.0 g, per 100 g of a raw material milk. The timing of addition is preferably before adding PG to a raw material milk or at the same time of adding PG to a raw material milk. However, it is possible to add a calcium chelating agent after addition of PG to a raw material milk unless the PG is deactivated. As for a calcium chelating agent, sodium citrate, sodium γ-polyglutamate or tetrasodium ethylenediaminetetraacetate is preferable. The salt form is preferable because these materials, when used other than in a salt form, tend to lower the pH and the raw material milk tends to become unstable and the reactivity becomes lower.

When adding an alkaline material, potassium carbonate, sodium carbonate, trisodium phosphate, sodium hydrogencarbonate, calcined calcium, and arginine as a food additive are encompassed as the alkaline material for the present invention. The raw material milk may be adjusted to pH 7 to 8 by adding the alkaline material. Therefore, the amount of addition of the alkaline material may be appropriately adjusted according to the selected alkaline material; however, it may be preferable to add 0.01 to 0.5 g, more preferably 0.04 to 0.5 g, per 100 g of a raw material milk. The timing of addition is preferably before adding PG to a raw material milk or at the same time of adding PG to a raw material milk. However, it is possible to add the alkaline material after addition of PG to a raw material milk unless the PG is deactivated. Or it may be possible to adjust the pH of a raw material milk to 7 to 8 by directly adding sodium hydroxide solution. After an enzyme reaction, the pH of the raw material milk may be left as it is, or may be back to the original value by using an acid.

When adding a reducing agent, thiol compounds such as a glutathione, cysteine, γ-glutamilcysteine or yeast extract containing the material in high concentration may be encompassed as the reducing agent, and preparations containing thereof are also encompassed. The amount of addition of the reducing agent is applied between 0.0001 to 0.1 g, preferably 0.001 to 0.01 g, per 100 g of raw material milk. When using yeast extract containing the material in high concentration, an amount of yeast extract containing 0.0001 to 0.1 g of reducing agent per 100 g of a raw material milk can be added to a raw material milk. When adding smaller amount of reducing agent than the range indicated above, it is hard to obtain the effect. On the other hand, when adding larger amount of reducing agent than the range, it may cause adverse influence to flavor and, in some cases, the effect to improve reactivity is no more enhanced even when the amount of addition is increased in excess of certain limit value. As to the timing of addition of a reducing agent to a raw material milk, it may be possible to add a reducing agent to a raw material milk in advance or after addition of PG unless the PG is deactivated. From the viewpoint of practical use, a reducing agent is added preferably at the same time of addition of PG. Also from the viewpoint of the effect of the reducing agent, preferably the reducing agent is added at the same time of addition of PG because when the reducing agent is incubated in a raw material milk for a long time, the intrinsic reducing power of a reducing agent may be decreased.

When fractioning and removing a low molecule fraction of a raw material milk, a method such as an ion exchange, electrodialysis, ultrafiltration (UF), reverse osmosis method, and the like may be preferable, which are industrially used in milk industries for fractioning and removing a low molecule fraction. Particularly, a method using an UF membrane for removing a low molecule fraction is preferable, by which water as a solvent and low molecule solutes are permeated and high molecule solutes such as proteins are kept. For example, it is efficient to remove a low molecule fraction using an UF membrane having a molecular weight of 10,000 to 20,000. A dialysis membrane may be used for an experimental use.

The inventors have found another method without using additives or fractioning for improving reactivity of a raw material milk. The method is control of the reaction temperature. The optimum temperature range for PG is, as described in Yamaguchi et al., *Eur. J. Biochem.*, vol. 268 pp. 1410-1421 (2001), which is incorporated herein by reference in its entirety, around 50 to 60° C.; however, the stability of PG decreases steeply from the temperature around over 50° C. According to the present invention, it was discovered that a difference of reactivity between a raw material milk having low heat history and UHT milk becomes small by reacting milk with PG at the temperature (range) of 60 to 65° C. that begins a steep decreasing of stability of PG. Thus the reaction does not need a long time but it takes a short time such as 5 to 60 minutes to finish the enzyme reaction.

The kind of the protein damidating enzyme used for the present invention is not limited as far as it possesses the function to act on amide group in a protein directly and cut a peptide bonding and deamidate the protein without linking. As an example of such an enzyme, a protein deamidating enzyme derived from *Chryseobacterium, Flavobacterium* or *Empedobacter* as disclosed in JP2000-50887A, JP2001-21850A, and WO2006/075772, which are incorporated herein by reference in their entireties; a protein glutaminase, commercially available in the market, derived from *Chryseobacterium*, and the like are exemplified but not limited to them. Preferably, an enzyme derived from *Chryseobacterium* is used. As for transglutaminase, it is not included in a protein deamidating enzyme according to the present invention because when acting transglutaminase on food materials, it brings mainly a cross-linking reaction in proteins and almost no deamidating reaction.

A protein deamidating enzyme can be prepared from a culture liquid for microorganism that produces the protein deamidating enzyme. Publicly known separation and purification methods of protein (such as centrifuging, UF concentration, salting-out, various kinds of chromatography with ion-exchanging resin, etc.) can be used as the preparation method of a protein deamidating enzyme. For example, culture liquid is centrifuged to separate bacterial cells, and then salting-out and chromatography, and the like may be combined to obtain target enzymes. When collecting enzymes from the interior of bacterial cells, the bacterial cells can be crushed by a pressure processing or ultrasonic processing, for example, and then separated and purified as described above to obtain target enzymes. Bacterial cells may be recovered from a culture liquid by filtration or centrifuge, etc. prior to the processing steps above explained (such as crushing of bacterial cells, separation and purification). The enzymes may be powdered by a drying method such as a freeze drying or vacuum drying, etc., and an appropriate diluent or drying auxiliary agent may be used at the drying step.

The activity of the protein deamidating enzyme is measured by the following steps according to the present invention:

(1) 100 μl of an aqueous solution containing the protein deamidating enzyme is added to 1 ml of 0.2 M phosphoric acid buffer solution (pH 6.5) containing 30 mM of Z-Gln-Gly (Peptide Institute, Inc.), and incubated for 10 minutes at 37° C., and then the reaction is ceased by adding 1 ml of 0.4 M TCA solution.

(2) An amount of ammonia produced by the reaction in a reacted solution of (1) is measured by using Ammonia-test-Wako (manufactured and retailed by Wako Pure Chemical Industries, Ltd.).

(3) A blank solution is measured at the same time. The blank solution is prepared such that a solution without the enzyme is incubated for 10 minutes at 37° C. and then 1 ml of 0.4 M TCA solution and 100 μl of an aqueous solution containing the protein deamidating enzyme are added in this order.

(4) The concentration of the enzyme is adjusted by diluting with a phosphoric acid buffer solution (pH 6.5) such that an absorbance at 630 nm becomes in the range of Δ0.2 to 0.8.

(5) The activity is measured by a unit (U) which indicates the amount of the enzyme that can produce one μmol of ammonium in one minute. The enzyme activity is calculated by a following expression.

$$\text{Enzyme activity (U/ml)} = (Es-Eb) * F * 0.123 \times Df$$

where;
Es: absorbance of a solution enzyme reacted,
Eb: absorbance of a blank,
F: factor (the reciprocal of the slope of a straight line of a calibration curve for standard ammonium solution), and
Df: dilution ratio of an enzyme solution.

According to the present invention, the amount of PG added is preferably 0.01 to 100 U per 1 g of milk protein in a raw material milk and more preferably 0.1 to 20 U. When adding 0.1 U or less, it is hard to obtain a desired result and when adding 20 U or more, an economical advantage becomes small. The reaction temperature can generally be set about 0 to about 65° C. and the reaction time may be set about 1 minute to about 40 hours. However, it is preferable to react for about 5 minutes to about 20 hours about at 5 to 65° C.

It is possible to adjust the degree of deamidation of milk protein by PG, that is, the degree of modification of milk according to material characteristics of required dairy products by controlling the amount of PG, reaction time, reaction temperature, and the like. An amount of ammonium produced by the deamidating reaction is measured for determining the degree of deamidation of milk protein. For ceasing the reaction, no limitation is required, and sterilization conditions used for manufacturing dairy products are generally employed. Of course, it is possible to obtain the effect of the present invention without such a sterilization process. The modified raw material milk obtained in this way is included as a dairy product produced by the method of the present invention. The dairy products having dense and creamy texture produced by the present invention which are produced from a raw material milk having low heat history, whose low reactivity with PG is improved, by treating with PG can be exemplified as follows. They are yoghurt, cheese, ice cream, condensed milk, defatted condensed milk, total powdered milk, powdered defatted milk, total milk protein, whey powder, lactic acid bacteria beverage, milk-based drink, and the like. In addition, processed foods, sort of like white source, added with a secondary ingredient such as salt, sugar, sweetener, spices, seasonings, etc. are included in the present invention.

Other features of the invention will become apparent in the course of the following descriptions of exemplary embodiments which are given for illustration of the invention and are not intended to be limiting thereof.

EXAMPLES

Experimental Example 1

Figure 1:
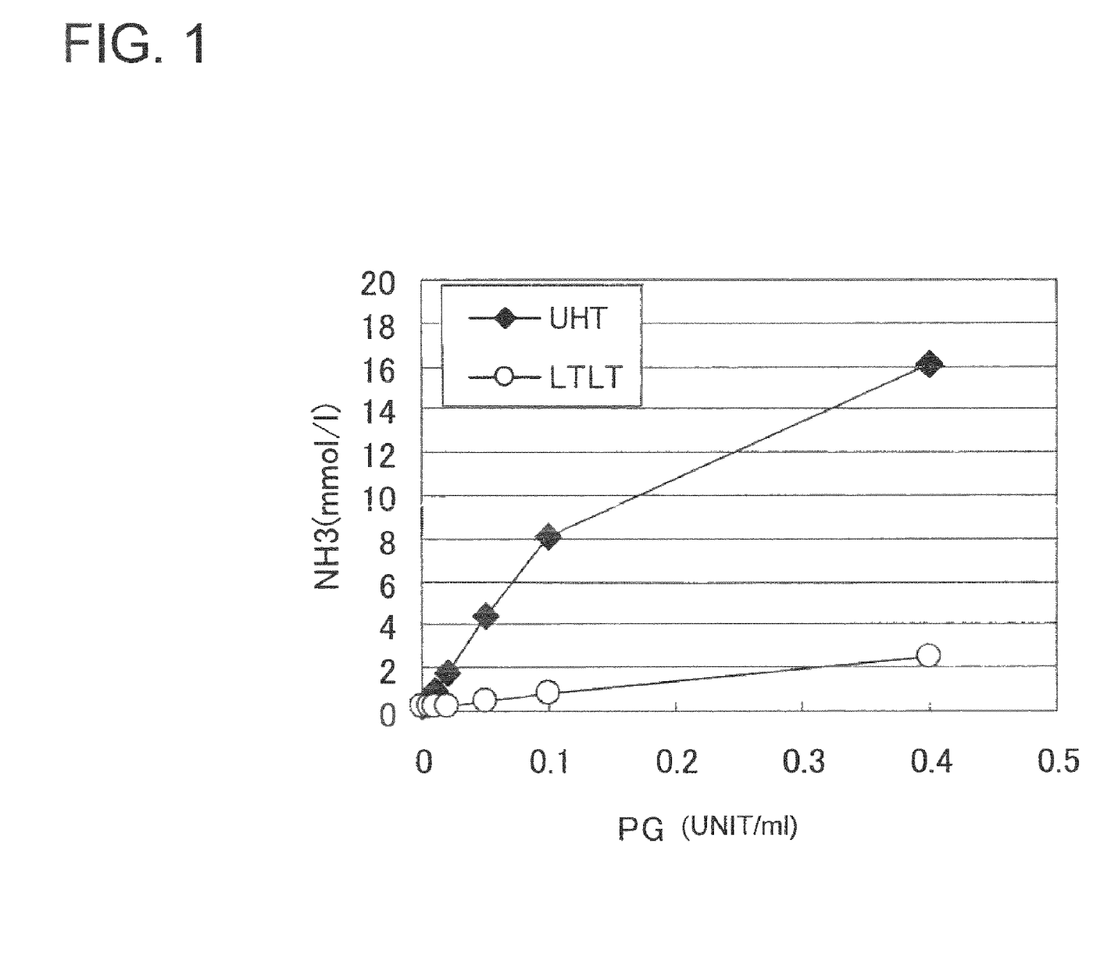
FIG. 1 is a graph showing reactivity of PG with LTLT milk and UHT milk (Experimental Example 1)

For confirming the difference of reactivity with PG between LTLT sterilized milk (66° C., 30 minutes: Takanashi low temperature sterilized milk) and UHT sterilized milk (130° C., 2 seconds: Magokoro Rakuno 3.6 milk), to each milk was added 0 to 0.4 U/ml of PG (purified product prepared by a method disclosed in *Appl. Microbiol. Biotechnol.*, (2008) 78: 67-74, which is incorporated herein by reference in its entirety, relative activity 120 U/mg-protein) and reacted at 50° C. for 60 minutes. As shown in FIG. 1, LTLT milk had low reactivity compared with UHT milk and obtained only one fifth to one fourth the amount of reaction by the same amount of enzyme. It is estimated that an inhibitor contained in a low molecule fraction in the milk is the cause as indicated by following Experimental Examples 2 to 4, and it is an object of the present invention to remove the inhibiting factor and improve reactivity of a raw material milk.

Experimental Example 2

The purified PG product described in Experimental Example 1 (50 U/ml) was diluted 100 times using following solvents (a) to (c). (a): 20 mM phosphoric acid buffer solution (pH 6.3), (b): LTLT sterilized milk (66° C., 30 minutes: Takanashi low temperature sterilized milk), (c): ultrafiltrte (Amicon, Centriprep YM-10; cut by molecular weight 10,000) of supernatant of supercentrifuge of (b). The activity of PG was measured by a method described above in the present specification using Z-Gln-Gly as a substrate and the results are shown in Table 1. When PG was diluted by a phosphoric acid buffer solution, the activity was 0.5 u/ml, and when diluted by LTLT sterilized milk, the activity lowered to about 12%. When PG was diluted by a low molecule fraction obtained by the ultrafiltration of LTLT sterilized milk, the activity disappeared completely. The results indicate that a PG inhibitor exists in LTLT sterilized milk, especially in the low molecule fraction.

TABLE 1

| Solvent for diluting enzyme | Activity (U/ml) | Relative activity (%) |
|---|---|---|
| (a) 20 mM phosphoric acid buffer solution | 0.501 | 100 |
| (b) low temperature sterilized milk | 0.062 | 12.3 |
| (c) ultrafiltrate of (b) | 0 | 0 |

Experimental Example 3

Next, an example will be explained, in which the PG activity recovers by treating the low molecule fraction obtained by ultrafiltration of LTLT sterilized milk with heat or a reducing agent. The purified PG product described in Experimental Example 2 (0.5 U/ml) was diluted by 100 times with ultrafiltrate treated with heat block at 90° C. for 5 minutes or 1.0 mM of reduced glutathione as a reducing agent (corresponding to 0.03 g per 100 g of a raw material milk). The PG activity was measured as in Experimental Example 2 and the results are shown in Table 2. The ultrafiltrate eliminated almost all of the PG activity; however, PG activity recovered drastically by heat treatment or adding a reducing agent. The same result was obtained when used casein micelle (precipitated pellet obtained by ultracentrifuge (Hitachi-Koki, Ltd., Himac CP80WX, 28,600 rpm, 60 min., 25° C.)) in milk instead of Z-Gln-Gly as a substrate (data not shown). The reactivity of casein micelle, as a main protein in raw material milk, with PG was good and it was confirmed that the low reactivity of PG was caused by solvent.

TABLE 2

| Solvent for enzyme dilution | Activity (U/ml) | Relative activity (%) |
|---|---|---|
| (1) 20 mM phosphoric acid buffer solution | 0.540 | 100 |
| (2) ultrafiltrate of low temperature sterilized milk | 0.016 | 2.96 |
| (3) (2) + heating (90° C., 5 minutes) | 0.432 | 80.0 |
| (4) (2) + 1 mM reduced glutathione | 0.552 | 102 |

Some methods will be explained as examples, which improve the PG reactivity with milk having low heat history by eliminating or reducing an inhibitor existing in a low molecule fraction of low temperature sterilized milk; however, the present invention is not limited by these examples.

Example 1

Calcium chelating materials were added to LTLT sterilized milk (66° C., 30 minutes: Takanashi low temperature sterilized milk) properly. The reactivity of PG with each milk sample was measured as follows. To each milk sample was added 0.4 U/ml (corresponding to about 12 u per 1 g of milk protein) of PG (a purified product described in Experimental Example 1) and incubated at 50° C. for 60 minutes. The enzyme reaction was ceased by adding 12% TCA the amount of which is the same as the reacting solution and centrifuged (12,000 rpm, 5° C., 5 minutes) to measure the amount of ammonium in the supernatant using an ammonium quantitative measurement kit, F-kit (Roche). The milk added with various calcium chelating materials increased the reactivity of PG compared with the milk not added with calcium chelating material (control) as shown in Table 3.

TABLE 3

| Additive | PG reactivity (%) |
|---|---|
| No additive added (control) | 22.1 |
| 20 mM EDTA | 55.9 |
| Trisodium citrate 0.2% | 40.5 |
| Trisodium citrate 0.4% | 47.3 |
| Trisodium citrate 0.5% | 42.8 |
| 0.4% γ-PGA | 49.8 |
| 0.5% γ-PGA | 58.1 |
| 0.75% γ-PGA | 79.2 |
| 1% γ-PGA | 96.1 |

Example 2

Alkaline materials were added to LTLT sterilized milk (66° C., 30 minutes: Takanashi low temperature sterilized milk) properly so as to adjust the pH 7 to 8.4. The reactivity of PG with each milk sample was measured as in Example 1. As shown in Table 4, the reactivity of PG to milk added with various alkaline materials increased depending on the value of pH compared with the milk without alkaline material (control).

TABLE 4

| Additive | Concentration | pH | PG reactivity (%) |
|---|---|---|---|
| No additive (control) | — | 6.67 | 13.6 |
| Potassium carbonate | 0.13% | 7.51 | 62.5 |
| Sodium carbonate | 0.10% | 7.38 | 61.7 |
|  | 0.15% | 7.87 | 72.7 |
|  | 0.20% | 8.38 | 65 |

TABLE 4-continued

| Additive | Concentration | pH | PG reactivity (%) |
|---|---|---|---|
| Trisodium phosphate | 0.15% | 7.41 | 54.9 |
| | 0.20% | 7.63 | 65.8 |
| | 0.25% | 7.94 | 72 |
| Sodium hydrogen carbonate | 0.30% | 7.22 | 58.1 |
| | 1.00% | 7.57 | 57.8 |
| calcined calcium | 0.04% | 7.32 | 54.9 |
| | 0.05% | 7.61 | 72.4 |
| | 0.06% | 7.92 | 83.1 |
| Arg (amino acid) | 0.20% | 7.24 | 54.1 |
| | 0.25% | 7.45 | 67 |
| | 0.30% | 7.69 | 76.2 |
| | 0.40% | 8.18 | 75 |

Example 3

Figure 2:
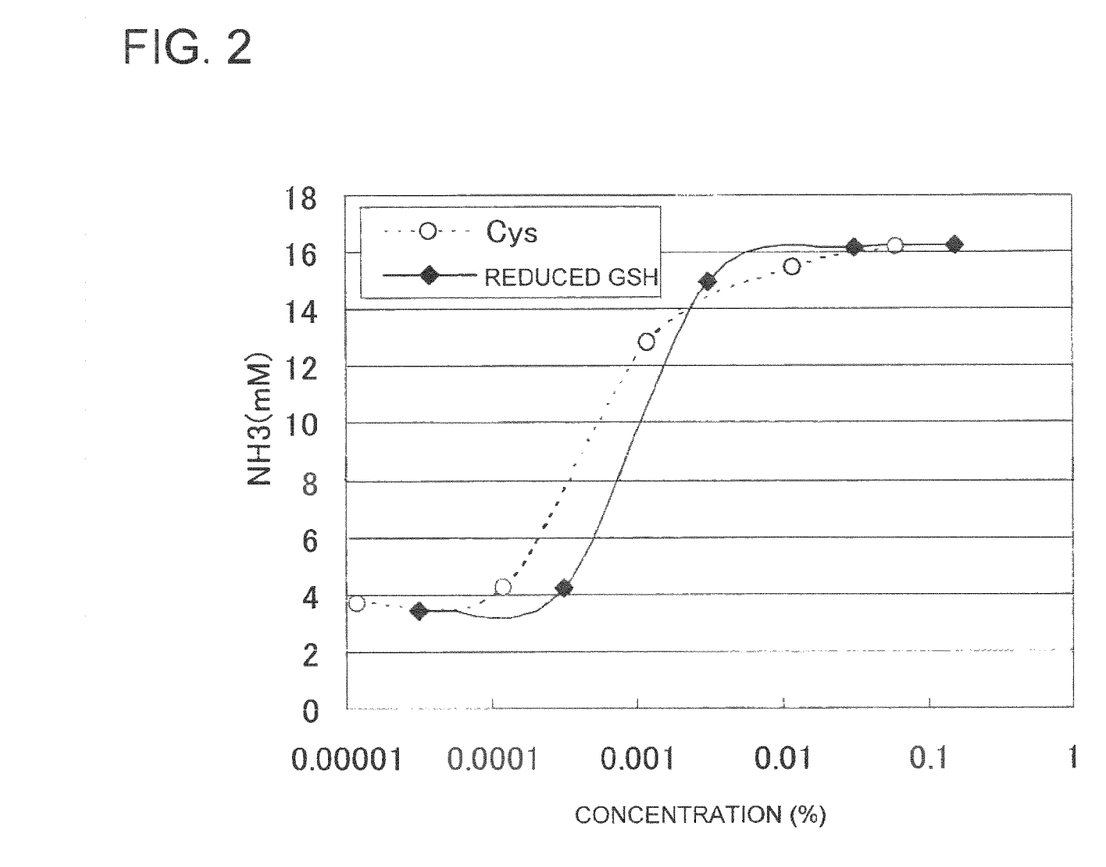
FIG. 2 is a graph showing reactivity of PG to milk that is added with a reducing agent (Example 3)
Figure 3:
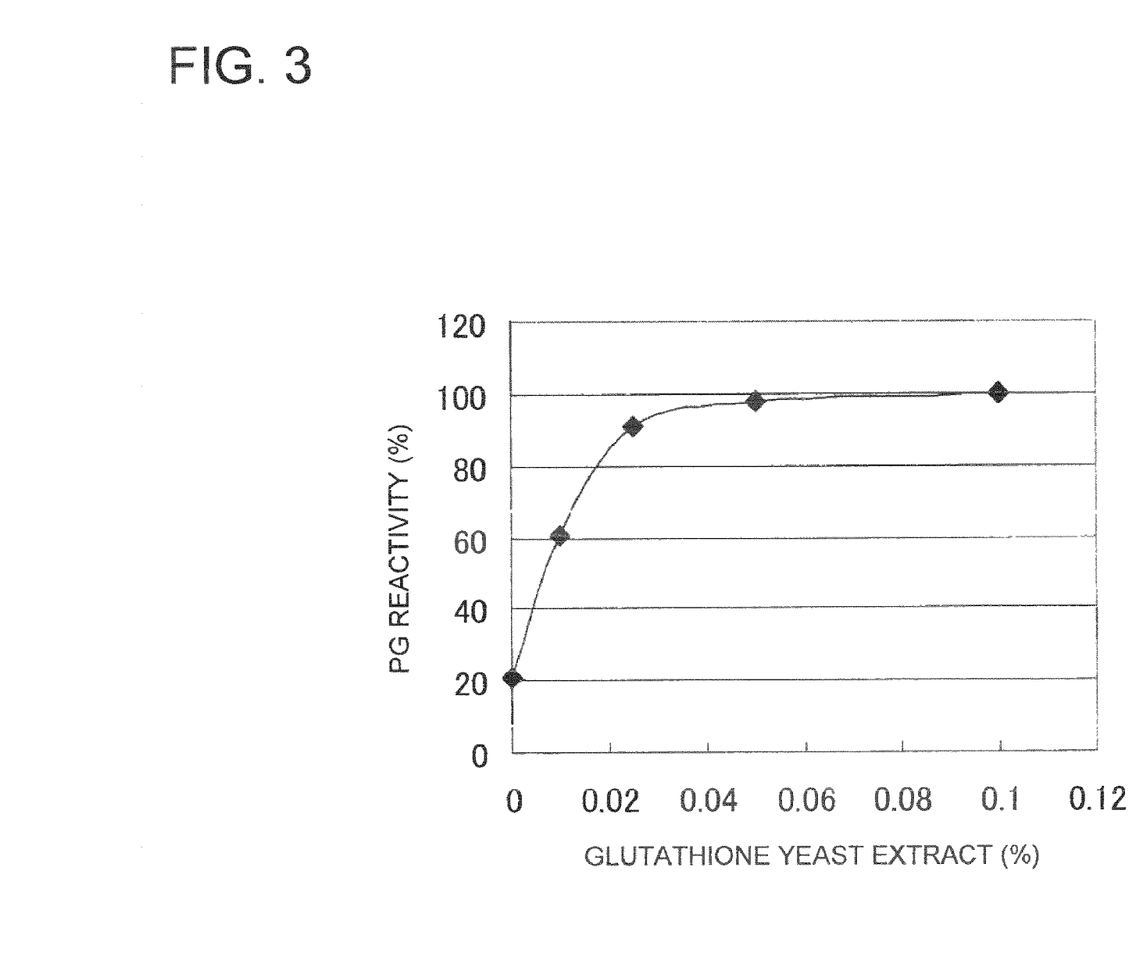
FIG. 3 is a graph showing reactivity of PG to milk that is added with yeast extract containing glutathione (Example 3)

Glutathione or cysteine (Nacalai Tesque, Inc.) as a thiol-type reducing agent was added to LTLT sterilized milk (66° C., 30 minutes: Takanashi low temperature sterilized milk) properly. The reactivity of PG to each milk was measured as in Example 1. As shown in FIG. 2, the reactivity of PG increased by both agents depending on the amount of addition and the reactivity recovered about 80 to 90% by adding the agent in 0.001%. By the same manner, the reactivity of PG to milk was measured by adding glutathione yeast extract (AROMILD UG8, Kohjin Co., Ltd.) to milk at different concentrations. As shown in FIG. 3, the reactivity recovered about 70% by 0.02% or more of the extract and almost 100% by 0.05% or more.

Example 4

Figure 4:
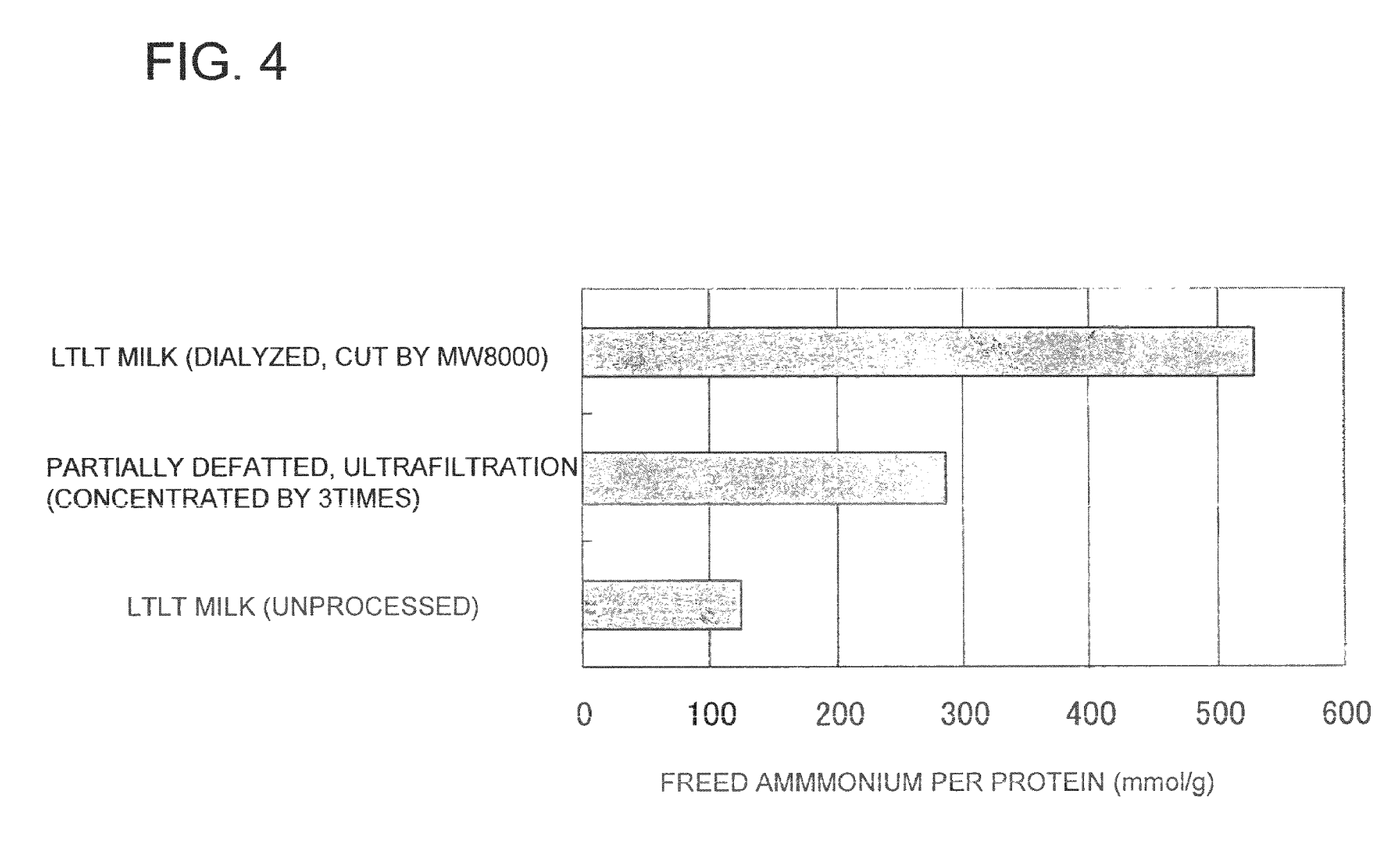
FIG. 4 is a graph showing reactivity of PG to milk from which a low molecule fraction has been removed (Example 4)

LTLT sterilized milk (66° C., 30 minutes: Takanashi low temperature sterilized milk) was centrifuged (8,000 rpm, 1 hour, 10° C.) to remove fat partially. The milk obtained was concentrated by about three times using an ultrafiltration membrane (Sartorius, Hydrosart membrane, cut by MW 10,000). The purified PG product described in Experimental Example 1 was added such that the amounts of addition of enzyme per milk protein become equal and the reactivity of PG was measured (reaction condition: 50° C., 1 hour). An amount of ammonium produced by the reaction was converted into that per protein and the reactivity was compared with each other. It was found that concentrated milk increased the reactivity by about three times as shown in FIG. 4. Furthermore, by dialyzing milk using a cellulose dialyzing membrane (cut by molecular weight 8,000) over one night at 4° C., the reactivity of PG increased more. The results showed that the reactivity increases by removing a low molecular fraction in milk.

Example 5

Figure 5:
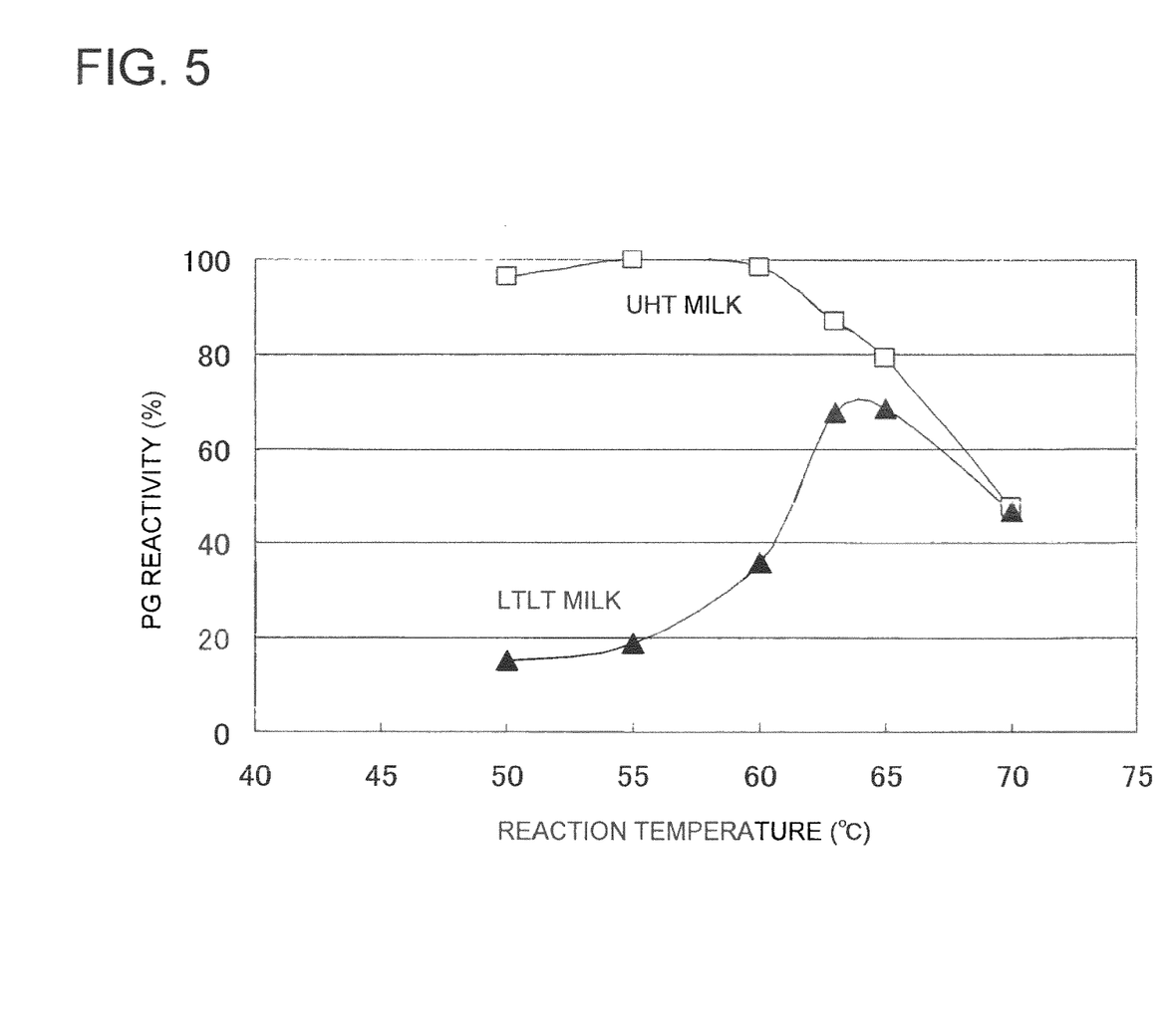
FIG. 5 is a graph showing a relation between reactivity of PG and reaction temperature of PG (Example 5)

A relation between temperature and the amount of reacted PG in a reaction between PG and LTLT sterilized milk (66° C., 30 minutes: Takanashi low temperature sterilized milk) was determined, and it was found that the relation was different from that of UHT milk as shown in FIG. 5. In a case using UHT milk, the reactivity reached its largest level at the temperature range of 50 to 60° C. and the reactivity declined linearly over 60° C. On the other hand, when using LTLT milk, it was found that the reactivity was lower than that of UHT milk in all of the temperature range; however, the reactivity increased sharply around the temperature of 60 to 65° C. and the reactivity recovered by 80 to 90% to that of UHT milk.

Example 6

According to the present invention, it is possible to provide dairy products of lower price and higher quality by using means to improve reactivity of a raw material milk having low heat history with PG. It will be explained that all means aforementioned can be applied to practical food by taking yoghurt as an example.

To LTLT sterilized milk (66° C., 30 minutes: Takanashi low temperature sterilized milk; milk protein 3.2%, milk fat 3.7%) were added the purified PG product described in Experimental Example 1 in an amount of 1 U per 1 g of milk protein in the raw material milk and trisodium citrate (a food additive) in an amount of 0.4% relative to the raw material milk at the same time and kept for 1 hour for reaction at 50° C. After that it was heated to 95° C. and kept for 1 minute for ceasing the reaction and sterilizing and then cooled down to 47° C. immediately. Commercially available lactic acid bacterium starter "Yo-Flex YC-370" (Chr. Hansen) was added by 0.0063% to the raw material milk, put into cases and fermented at 44° C. until the pH became in the range of 4.5 to 4.6 to make yoghurt (sample of the present invention). Some control samples were prepared in the same manner for comparison. They are, a sample that was simply incubated for 1 hour at 50° C. (control sample 1), a sample that was mixed with trisodium citrate by 0.4% to a raw material milk and incubated for 1 hour at 50° C. (control sample 2), and a sample that was added with PG by 3.5 U to 1 g of milk protein and incubated for 1 hour at 50° C. (control sample 3). They were kept under refrigeration (at 5° C.) and physical properties (breaking area and adhesiveness) after 1 day were measured. A texture analyzer (Stable Macro Systems, LTD) was used and the test conditions were; test speed 1 mm/s, plate-type plunger having a diameter of 10 mm, and 10% compression. In addition, a sensory test was performed by five trained panelists. The results are shown in Table 5.

TABLE 5

| | Conditions | Treatment | Breaking area | Adhesiveness | Sensory test (comment) |
|---|---|---|---|---|---|
| Control sample 1 | 50° C., 1 hour | No additive | 20.6 ± 0.63 | 4.85 ± 0.33 | — |
| Control sample 2 | 50° C., 1 hour | Trisodium citrate 0.4% | 15.8 ± 0.31 | 5.62 ± 0.40 | Softer than control sample 1 |
| Control sample 3 | 50° C., 1 hour | PG (3.5 u/gp) | 20.0 ± 0.39 | 5.06 ± 0.37 | Not so different from control sample 1 |
| Present invention | 50° C., 1 hour | Trisodium citrate 0.4% + PG (3.5 u/gp) | 7.84 ± 0.21 | 7.05 ± 1.5 | Much softer than control samples 1 or 2 and smooth (creamy) |

Example 7

To LTLT sterilized milk (66° C., 30 minutes: Takanashi low temperature sterilized milk; milk protein 3.2%, milk fat 3.7%) were added the purified PG product described in Experimental Example 1 in an amount of 1 U per 1 g of milk protein and the AROMILD UG8 (Kohjin Co., Ltd., glutathione yeast extract, hereinafter called as "YE") in an amount of 0.01% and 0.02% relative to the raw material milk (contents of GSH relative to 100 g of the raw material milk are about 0.0007 g and 0.0014 g, respectively) at the same time and stirred for 1 hour for reaction at 50° C. After that they were heated to 95° C. and kept for 1 minute for ceasing the reaction and sterilizing the raw material milk and then cooled down to 47° C. immediately. Commercially available lactic acid bacterium starter "Yo-Flex YC-370" (Chr. Hansen) was added by 0.0063% to the raw material milk, put into cases and fermented at 44° C. until their pH became 4.5 to 4.6 to make yoghurt (samples 1 and 2 of the present invention). Comparative yoghurts were prepared in the same way for comparison by adding no PG nor YE (control sample 1) and by adding PG only (control sample 2). It has been confirmed that samples obtained by adding YE only by 0.01% and 0.02% render the results almost the same as the control sample 1. After fermentation, they were kept under refrigeration (at 5° C.) and the physical properties (breaking area and adhesiveness) after 1 day were measured. The methods for the measurement of physical properties and the sensory test are the same as explained in Example 6.

Figure 6:
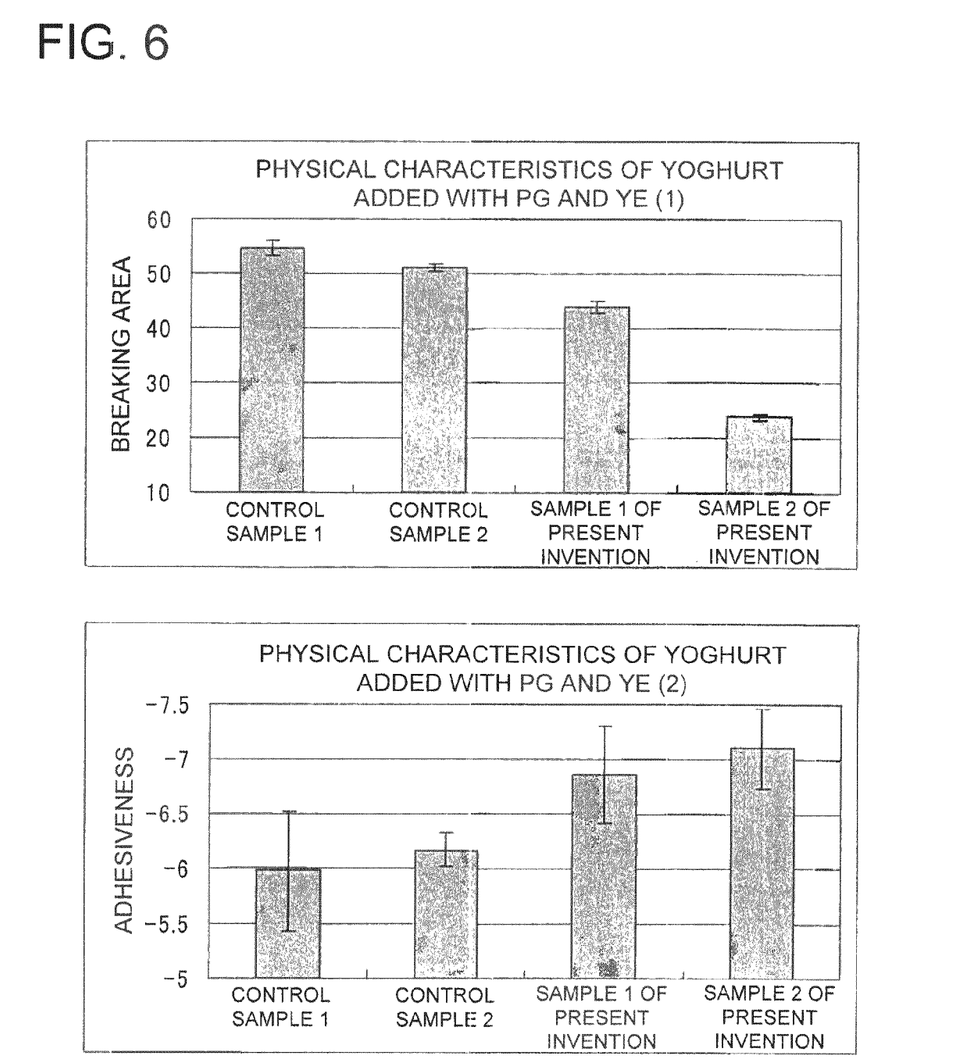
FIG. 6 shows results of measurements of physical properties of yoghurt (Example 6).

As indicated by the results (FIG. 6) of the physical properties measurements, the sample added with PG only (control sample 2) showed little difference from the additive-free sample (control sample 1). On the other hand, a decrease in breaking area and an increase in adhesiveness were clearly observed from the samples 1 and 2 of the present invention. This means that the physical properties of yoghurt became soft and creamy and the results correspond to the results of the sensory test shown in Table 6. As a result, it has been proved that an effect of PG larger than before can be obtained by addition of the glutathione yeast extract and that the effect can be controlled by an amount of the extract to be added.

TABLE 6

| | Comment |
|---|---|
| Control sample 1 | — |
| Control sample 2 | Little difference from control sample 1 |
| Present invention 1 | Softer than control sample 1 and creamy texture |
| Present invention 2 | Still softer than present invention 2 [sic. 1] and creamy texture |

Example 8

LTLT sterilized milk (66° C., 30 minutes: Takanashi low temperature sterilized milk; milk protein 3.2%, milk fat 3.7%) was partially defatted by centrifuge (8,000 rpm, 1 hour, 10° C.) and then concentrated by 4 times using ultrafiltration membrane (Sartorius, Hydrosart membrane, cut by MW 10,000) to obtain viscous condensed milk. The purified PG product described in Experimental Example 1 was added thereto in an amount of 8 U per 1 g of milk protein and reacted at 50° C. for 60 minutes. The condensed milk curdled, and very dense and smooth cheese-like food was obtained. A condensed milk to which no PG was added was also reacted for comparison; however, the condensed milk did not curdle and remained in a liquid state. As explained above, a condensed milk obtained by desalinating condensation can be treated with PG effectively for making cheese-like dairy products having smooth texture.

Example 9

To LTLT sterilized milk (66° C., 30 minutes: Takanashi low temperature sterilized milk; milk protein 3.2%, milk fat 3.7%) was added the purified PG product described in Experimental Example 1 in an amount of 10 U per 1 g of milk protein and reacted at 65° C. for 60 minutes. The reacted milk was heated to 85° C. in a boiling water bath to deactivate the enzyme and then cooled rapidly to make deamidated milk (experimental sample (a)). A sample obtained in the same way except that no enzyme was added (experimental sample (b)) and a sample obtained by adding the purified PG product to the LTLT sterilized milk in an amount of 10 U per 1 g of milk protein and reacting at 50° C. for 60 minutes (experimental sample (c)) were also prepared for comparison. The concentrations of ammonium in the milk after reaction were 11.1 mmol/l in the experimental sample (a), 0.12 mmol/l in the experimental sample (b) and 2.05 mmol/l in the experimental sample (c).

100 g of egg (corresponding to about 2 eggs) and 30 g of sugar were mixed and stirred and added with the experimental samples (a) to (c) that were heated to about 40° C. They were poured into aluminum cups through a chinois and heated in a steamer over a medium flame for 15 minutes. After that they were cooled, refrigerated for one day and used for a sensory test (n=3). As shown in Table 7, compared with puddings (comparative samples 1 and 2) made from the milk of experimental samples (b) and (c), a pudding (of the present invention) made from the milk of experimental sample (a) showed the strongest yellow color of an egg and smooth cross section having few pores. The texture was favorable because it was very smooth and could feel more milk flavor. The quality of pudding depends on kinds of milk used, and pudding using low temperature sterilized milk is popular because we can enjoy unspoiled natural flavor of the raw milk. According to the present invention, it has been confirmed that a pudding having rich flavor and smooth texture can be produced by setting the reaction temperature of LTLT milk with PG at 65° C. for keeping the high reactivity of PG.

TABLE 7

| | | Free comment (n = 3) |
|---|---|---|
| Experimental sample (a) | Sample of the Present invention | More yellowish than comparative sample 1 and 2 Smooth texture, smooth touch at inserting a spoon, and smooth cross section with few pores. Weak smell of the white of egg, feel milk flavor (feel much yellow of an egg) |
| Experimental sample (b) | Comparative sample 1 | Slightly whitish Somewhat hard (as hard as white of boiled egg) Strong smell of the white of egg, weak milk flavor |
| Experimental sample (c) | Comparative sample 2 | Almost no difference from comparative sample 1 |

Example 10

Milked raw milk was defatted by a separator at 40° C. The defatted milk was sterilized in high temperature and short time (HTST) (75° C., 15 seconds) using a plate sterilizer. The resultant defatted milk was pre-incubated at 55° C. and a glutathione-containing yeast extract (Kohjin Co., Ltd., AROMILD UG8) was added in an amount of 0.02% (w/v) to the milk and at the same time PG (protein glutaminase, Amano Enzyme Inc.) was added in amounts of 1.5, 4.5 and 15 units (hereinafter the unit is designated as "u/gp") per 1 g of milk protein and reacted for one hour. The milk was heated up to 80° C. in a hot water bath to deactivate the enzyme (sample of the present invention). A sample added with PG in amounts of 1.5, 4.5 and 15 u/gp without adding the glutathione-containing yeast extract by 0.02% (w/v) to the milk was prepared for reference (control sample). Another sample was prepared for comparison for which HTST sterilized (75° C., 15 seconds) defatted milk was additionally heated (up to 95° C.) and added with PG in amounts of 1.5, 4.5 and 15 u/gp and reacted at 55° C. for one hour (comparative sample). Amount of ammonium produced by the reaction was measured for each of the control sample, the sample of the present invention and the comparative sample. When no PG was added, an amount of ammonium in the milk was 0.38, 0.38 and 0.34 mM for the control sample, the sample of the present invention and the comparative sample, respectively. On the other hand, when the same amount of PG was added, an amount of ammonium produced in the sample of the present invention was apparently larger compared with the control sample and the amount of reaction was almost the same as that of the comparative sample as shown in Table 8. The results indicate that it is possible to increase the reactivity of PG without additional heat treatment by adding a glutathione-containing yeast extract by 0.02% (w/v) to the milk.

TABLE 8

| | Amount of ammonium produced (mM) | | |
|---|---|---|---|
| PG (u/gp) | Control sample | Sample of the present invention | Comparative sample |
| 1.5 | 1.96 | 3.71 | 3.60 |
| 4.5 | 5.74 | 10.15 | 9.96 |
| 15 | 13.88 | 15.85 | 16.13 |

Control sample: defatted milk (HTST treatment), no addition.
Sample of the present invention: defatted milk (HTST treatment), high-glutathione-content yeast extract, AROMILD 0.02% added.
Comparative sample: defatted milk (HTST treatment, heat treatment up to 95° C.), no addition.

Example 11

The defatted milk of the present invention prepared by the method of Example 10 was powdered by a spray-dry method. A weakly acidic milk-based drink was prepared using the defatted powdered milk according to the composition of Table 9. Water was measured by a jug and the defatted powdered milk and granulated sugar were added to the measured water and dissolved, and 10% solution of citric acid (anhydrous) was dropped with stirring by 3,000 rpm using TK Robomix (Tokushu Kika Kogyo, K.K.). Immediately, the rotating speed was increased and the solution was stirred for 3 minutes at 8,000 rpm to dissolve completely. The resultant solution was poured into a heat-resistant PET bottle (500 ml volume) for fraction and heat-treated up to 96° C. After that it was checked whether or not precipitation occurred. As shown in Table 10, precipitation occurred in the drink made by defatted powdered milk without treating with PG and the drink treated with PG by 1.5 u/gp. However, precipitation was remarkably suppressed in the drinks treated with PG by 4.5 u/gp and 15 u/gp and the solutions kept dispersed. The final pH values of the samples of the present invention were 5.2 to 5.3 compared with the control sample the pH of which was 5.09. Although the amount of citric acid added was the same, the pH value after dissolution of the sample of the present invention was higher by 0.2 to 0.3 than that of the sample without treating. The fact revealed that the defatted powdered milk prepared by the present invention has high buffer capacity.

TABLE 9

| Material | Composition (%) |
|---|---|
| Defatted powdered milk | 3.2% |
| Granulated sugar | 5.0% |
| 10% wt citric acid (anhydrous) | 1.15% |
| water | 90.65% |
| | 100% |

TABLE 10

| | PG (u/gp) | Final pH | Precipitation after heating |
|---|---|---|---|
| Control sample | 0 | 5.09 | much X |
| Comparative sample | 1.5 | 5.18 | much X |
| Present invention 1 | 4.5 | 5.28 | little ○ |
| Present invention 2 | 15 | 5.32 | almost zero ◎ |

Next, an effect of pH of the milk-based drinks for preventing the precipitation was tested using defatted powdered milk of the control sample and the sample 2 (treated with PG by 15 u/gp) of the present invention. The amount of citric acid was adjusted so as to make the pH between 5.0 and 5.6 based on Table 10 and water was added so as to make the total weight to 100%. After preparation, the solutions were poured into heat-resistant PET bottles and heat-treated up to 96° C. As shown in Table 11, the control sample drinks before heating were dispersed and white at the pH of 5.55 and 5.63; however, they precipitated and aggregated after heating. On the other hand, as for the sample drinks of the present invention, the precipitation was remarkably suppressed at the pH of 5.2 or more regardless of heat treatment. As can be seen by the results of the control sample drinks, generally the stability of milk protein in the weak acidity range is low. However, it has been proved that the stability of the defatted powdered milk can be remarkably improved by previously treating with PG as shown by the sample of the present invention. The results suggest that the present invention is useful for making milk-based drinks containing coffee, weakly acidic milk-based drinks containing fruit, and the like.

TABLE 11

| | Control sample drink | | Sample 2 of the present invention | |
|---|---|---|---|---|
| pH | Before heating | After heating | Before heating | After heating |
| 5.06 | X | X | X | X |
| 5.11 | — | — | X | X |
| 5.20 | X | X | ○ | ○ |
| 5.24 | — | — | ◎ | ○ |
| 5.33 | X | X | ◎ | ◎ |
| 5.48 | X | X | — | — |
| 5.55 | ◎ | X | — | — |
| 5.63 | ◎ | X | — | — |

INDUSTRIAL APPLICABILITY

According to the present invention, it is possible to obtain modified milk by using a protein deamidating enzyme effectively even with a raw material milk having low heat history, such as raw milk, that has low reactivity with a protein deamidating enzyme. In addition, by using the modified milk as a raw material milk, it is possible to produce dairy products having dense and creamy texture. Thus the present invention is very useful in the food field.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for producing modified milk, comprising:
   treating a raw material milk selected from the group consisting of raw milk, LTLT sterilized milk, and HTST sterilized milk to reduce an inhibitor of a protein deamidating enzyme; and
   treating said raw material milk with a protein deamidating enzyme,
   wherein said treating to reduce an inhibitor of a protein deamidating enzyme comprises addition of a calcium chelating agent to said raw material milk in an amount of 0.2 to 1.0 g per 100 g of the raw material milk.

2. A method according to claim 1, wherein said calcium chelating agent is one or more selected from the group consisting of sodium citrate, sodium γ-polyglutamate, tetrasodium ethylenediaminetetraacee, and a mixture thereof.

3. A method for producing modified milk, comprising:
   treating a raw material milk selected from the group consisting of raw milk, LTLT sterilized milk, and HTST sterilized milk to reduce an inhibitor of a protein deamidating enzyme; and
   treating said raw material milk with a protein deamidating enzyme,
   wherein said treating to reduce an inhibitor of a protein deamidating enzyme comprises addition of an alkaline material to said raw material milk in an amount of 0.01 to 0.5 g per 100 g of said raw material milk.

4. A method according to claim 3, wherein said alkaline material is one or more selected from the group consisting of sodium hydroxide, potassium carbonate, sodium carbonate, trisodium phosphate, sodium hydrogencarbonate, calcined calcium, arginine, and a mixture thereof.

5. A method for producing modified milk, comprising:
   treating a raw material milk selected from the group consisting of raw milk, LTLT sterilized milk, and HTST sterilized milk to reduce an inhibitor of a protein deamidating enzyme; and
   treating said raw material milk with a protein deamidating enzyme,
   wherein said treating to reduce an inhibitor of a protein deamidating enzyme comprises addition of a reducing material to said raw material milk in an amount of 0.0001 to 0.1 g per 100 g of said raw material milk or addition of yeast extract containing a reducing agent in an amount of 0.0001 to 0.1 g per 100 g of said raw material milk.

6. A method according to claim 5, wherein said reducing material is one or more selected from the group consisting of gluhione, cysteine, γ-glutamilcysteine, and a mixture thereof.

7. A method for producing modified milk, comprising:
   treating a raw material milk selected from the group consisting of raw milk, LTLT sterilized milk, and HTST sterilized milk to reduce an inhibitor of a protein deamidating enzyme; and
   treating said raw material milk with a protein deamidating enzyme,
   wherein said treating to reduce an inhibitor of a protein deamidating enzyme comprises removal of a low molecular weight fraction, having a molecular weight of 10,000 or less, from said raw material milk.

8. A method according to claim 7, wherein said removal of said low molecular weight fraction is performed using an ultrafiltration membrane.

9. A method for producing a dairy product, comprising converting modified milk prepared by a method according to claim 1 to said dairy product.

10. A method according to claim 9, wherein said dairy product is selected from the group consisting of yoghurt, a cheese-like food, pudding, and a milk-based drink.

11. A method according to claim 1, wherein said treating to reduce an inhibitor of a protein deamidating enzyme is commenced prior to commencement of said treating said raw material milk with a protein deamidating enzyme.

12. A method according to claim 1, wherein said treating said raw material milk with a protein deamidating enzyme is commenced prior to commencement of said treating to reduce an inhibitor of a protein deamidating enzyme.

13. A method according to claim 1, wherein said treating said raw material milk with a protein deamidating enzyme and said treating to reduce an inhibitor of a protein deamidating enzyme are commenced at the same time.

14. A method according to claim 1, wherein said treating said raw material milk with a protein deamidating enzyme and said treating to reduce an inhibitor of a protein deamidating enzyme are conducted at the same time.

15. A method for producing a dairy product, comprising converting a modified milk prepared by a method according to claim 3 to said dairy product.

16. A method according to claim 15, wherein said dairy product is selected from the group consisting of yoghurt, a cheese-like food, pudding, and a milk-based drink.

17. A method for producing a dairy product, comprising converting a modified milk prepared by a method according to claim 5 to said dairy product.

18. A method according to claim 17, wherein said dairy product is selected from the group consisting of yoghurt, a cheese-like food, pudding, and a milk-based drink.

19. A method for producing a dairy product, comprising converting a modified milk prepared by a method according to claim 7 to said dairy product.

20. A method according to claim 19, wherein said dairy product is selected from the group consisting of yoghurt, a cheese-like food, pudding, and a milk-based drink.

21. A method according to claim 3, wherein said treating to reduce an inhibitor of a protein deamidating enzyme is commenced prior to commencement of said treating said raw material milk with a protein deamidating enzyme.

22. A method according to claim 3, wherein said treating said raw material milk with a protein deamidating enzyme is commenced prior to commencement of said treating to reduce an inhibitor of a protein deamidating enzyme.

23. A method according to claim 3, wherein said treating said raw material milk with a protein deamidating enzyme and said treating to reduce an inhibitor of a protein deamidating enzyme are commenced at the same time.

24. A method according to claim 3, wherein said treating said raw material milk with a protein deamidating enzyme and said treating to reduce an inhibitor of a protein deamidating enzyme are conducted at the same time.

25. A method according to claim 5, wherein said treating to reduce an inhibitor of a protein deamidating enzyme is commenced prior to commencement of said treating said raw material milk with a protein deamidating enzyme.

26. A method according to claim 5, wherein said treating said raw material milk with a protein deamidating enzyme is commenced prior to commencement of said treating to reduce an inhibitor of a protein deamidating enzyme.

27. A method according to claim 5, wherein said treating said raw material milk with a protein deamidating enzyme and said treating to reduce an inhibitor of a protein deamidating enzyme are commenced at the same time.

28. A method according to claim 5, wherein said treating said raw material milk with a protein deamidating enzyme and said treating to reduce an inhibitor of a protein deamidating enzyme are conducted at the same time.

29. A method according to claim 7, wherein said treating to reduce an inhibitor of a protein deamidating enzyme is commenced prior to commencement of said treating said raw material milk with a protein deamidating enzyme.

30. A method according to claim 7, wherein said treating said raw material milk with a protein deamidating enzyme is commenced prior to commencement of said treating to reduce an inhibitor of a protein deamidating enzyme.

31. A method according to claim 7, wherein said treating said raw material milk with a protein deamidating enzyme and said treating to reduce an inhibitor of a protein deamidating enzyme are commenced at the same time.

32. A method according to claim 7, wherein said treating said raw material milk with a protein deamidating enzyme and said treating to reduce an inhibitor of a protein deamidating enzyme are conducted at the same time.

* * * * *